(12) United States Patent  
Sekiguchi et al.

(10) Patent No.: US 8,219,859 B2  
(45) Date of Patent: Jul. 10, 2012

(54) MEDICAL SUPPORT CONTROL SYSTEM

(75) Inventors: Kiyoshi Sekiguchi, Tokyo (JP); Masaru Ito, Yokohama (JP); Koichi Tashiro, Sagamihara (JP); Nobuyuki Furukawa, Tokyo (JP)

(73) Assignee: Olympus Medical Systems Corp. (JP)

( * ) Notice: Subject to any disclaimer, the term of this patent is extended or adjusted under 35 U.S.C. 154(b) by 334 days.

(21) Appl. No.: 12/033,083

(22) Filed: Feb. 19, 2008

(65) Prior Publication Data

US 2009/0210754 A1     Aug. 20, 2009

(51) Int. Cl.
*G06F 11/00* (2006.01)
(52) U.S. Cl. .......................................... 714/57
(58) Field of Classification Search .................. 714/57
See application file for complete search history.

(56) References Cited

U.S. PATENT DOCUMENTS

| | | | |
|---|---|---|---|
| 2004/0078724 A1* | 4/2004 | Keller et al. | 714/48 |
| 2004/0117563 A1* | 6/2004 | Wu et al. | 711/150 |
| 2004/0212607 A1* | 10/2004 | Tomiyasu | 345/204 |
| 2005/0097191 A1* | 5/2005 | Yamaki et al. | 709/219 |
| 2005/0108462 A1* | 5/2005 | Choi et al. | 711/5 |
| 2005/0283138 A1 | 12/2005 | Tashiro et al. | |
| 2005/0284491 A1 | 12/2005 | Tashiro et al. | |

FOREIGN PATENT DOCUMENTS

| | | |
|---|---|---|
| EP | 1 825 802 A1 | 8/2007 |
| EP | 1 929 933 A2 | 6/2008 |
| JP | 2005-110032 | 4/2005 |
| JP | 2005-334090 | 12/2005 |
| JP | 2006-000536 | 1/2006 |
| WO | WO 2005/119493 A | 12/2005 |

OTHER PUBLICATIONS

Partial European Search Report dated May 20, 2009 in corresponding European Patent Application No. EP 09 00 1421 (English-language).
Extended European Search Report dated Aug. 6, 2009 in corresponding European Patent Application No. EP 09 00 1421 (English language).

* cited by examiner

*Primary Examiner* — Scott Baderman
*Assistant Examiner* — Jigar Patel
(74) *Attorney, Agent, or Firm* — Ostrolenk Faber LLP

(57) ABSTRACT

A medical support control system comprising: a first controller connected to at least one device; a second controller connected to at least one device; and a manipulation display device shared by the first controller and the second controller, and alternately displaying a first graphical user interface (first GUI) created by the first controller and a second graphical user interface (second GUI) created by the second controller, wherein: first error information that is error information obtained from the first controller side and second error information that is error information obtained from the second controller side are shared by the first and second controllers, and are reflected on the first and second GUIs on the basis of the first and second error information.

4 Claims, 11 Drawing Sheets

ERROR LEVEL

| LEVEL | PRIORITY ORDER | OUTLINE |
|---|---|---|
| LEVEL S | 1 | CRITICAL ERROR THAT REQUIRES TURN-OFF OF SYSTEM |
| LEVEL A | 2 | WARNING LEVEL |
| LEVEL B | 3 | CAUTION LEVEL |

FIG.7

SAMPLE OF THE ERROR INFORMATION OUTPUT TABLE

| No. | ERROR ID | ERROR LEVEL | ERROR HEADER INFORMATION | DETAILED ERROR INFORMATION | |
|---|---|---|---|---|---|
| 1 | XXX1 | A | CLOG IN TUBE OF INSUFFLATION DEVICE | * * * * * | |
| 2 | XXX2 | A | OUTPUT ERROR IN ELECTRICAL SURGICAL DEVICE | * * * * * | |
| 3 | XXX3 | A | PC CARD ERROR OF CAMERA | * * * * * | ←ERROR DISPLAYED CURRENTLY |
| 4 | XXX4 | A | WB ERROR OF CAMERA | * * * * * | |

CASE 1: LEVEL S ERROR IS NEWLY CAUSED WHEN LEVEL A ERROR IS BEING DISPLAYED

| No. | ERROR ID | ERROR LEVEL | ERROR HEADER INFORMATION | DETAILED ERROR INFORMATION | |
|---|---|---|---|---|---|
| 1 | XX5 | S | DISORDER OF ** | * * * * * | ←ERROR DISPLAYED CURRENTLY |
| 2 | XX1 | A | CLOG IN TUBE OF INSUFFLATION DEVICE | * * * * * | |
| 3 | XX2 | A | OUTPUT ERROR IN ELECTRICAL SURGICAL DEVICE | * * * * * | |
| 4 | XX3 | A | PC CARD ERROR OF CAMERA | * * * * * | |
| 5 | XX4 | A | WB ERROR OF CAMERA | * * * * * | |

CASE 2: LEVEL A ERROR IS NEWLY CAUSED WHEN LEVEL A ERROR IS BEING DISPLAYED

| No. | ERROR ID | ERROR LEVEL | ERROR HEADER INFORMATION | DETAILED ERROR INFORMATION | |
|---|---|---|---|---|---|
| 1 | XX1 | A | CLOG IN TUBE OF INSUFFLATION DEVICE | * * * * * | |
| 2 | XX2 | A | OUTPUT ERROR IN ELECTRICAL SURGICAL DEVICE | * * * * * | |
| 3 | XX6 | A | VTR TAPE DOES NOT EXIST | * * * * * | ←ERROR DISPLAYED CURRENTLY |
| 4 | XX3 | A | PC CARD ERROR OF CAMERA | * * * * * | |
| 5 | XX4 | A | WB ERROR OF CAMERA | * * * * * | |

CASE 3: LEVEL B ERROR IS NEWLY CAUSED WHEN LEVEL A ERROR IS BEING DISPLAYED

| No. | ERROR ID | ERROR LEVEL | ERROR HEADER INFORMATION | DETAILED ERROR INFORMATION | |
|---|---|---|---|---|---|
| 1 | XX1 | A | CLOG IN TUBE OF INSUFFLATION DEVICE | * * * * * | |
| 2 | XX2 | A | OUTPUT ERROR IN ELECTRICAL SURGICAL DEVICE | * * * * * | |
| 3 | XX3 | A | PC CARD ERROR OF CAMERA | * * * * * | ←ERROR DIEPLAYED CURRENTLY |
| 4 | XX4 | A | WB ERROR OF CAMERA | * * * * * | |
| 5 | XX7 | B | ** OUTPUT + 1 | * * * * * | |

FIG.8

MEDICAL SUPPORT CONTROL SYSTEM

BACKGROUND OF THE INVENTION

1. Field of the Invention

The present invention relates to a medical support control system for controlling medical devices and non-medical devices used for operations.

2. Description of the Related Art

Operating systems using medical controllers or the like for controlling medical devices such as endoscopes or the like used for operations have been proposed. Medical devices to be controlled such as electric knives, insufflation devices, endoscope cameras, light source devices, or the like are connected to the medical controller (also referred to as an MC). Also, a display device, a manipulation panel, or the like is connected to the MC. The manipulation panel includes a display unit and a touch sensor, and is used as a central manipulation device by nurses, or the like working in an unsterilized area. The display device is used for displaying endoscope images or the like.

There is audio-visual equipment in the operating room, such as a room light, a room camera, an interphone device, a liquid crystal display device, or the like (non-medical devices). The audio-visual equipment is controlled independently or by a non-medical controller (also referred to as an NMC) used for the central control.

Japanese Patent Application Publication No. 2006-000536, for example, discloses an operating system, comprising:

a first controller connected to a medical device provided in an operating room;

a second controller connected to a non-medical device provided in the operating room; and manipulation instruction input means transmitting to the first controller content of a manipulation instruction when a manipulation instruction for the medical device and the non-medical device is input. The first controller transmits to the second controller a first control signal in accordance with the manipulation instruction of the non-medical device input into the manipulation instruction means. The second controller converts the first control signal into a second control signal used for controlling the non-medical device, and transmits the second control signal to the non-medical device. Thereby, the operating system and a non-medical system work together, and the operating person himself/herself or the like can manipulate the non-medical devices.

SUMMARY OF THE INVENTION

The medical support control system according to the present invention comprises:

a first controller connected to at least one device;

a second controller connected to at least one device; and a manipulation display device shared by the first controller and the second controller, and alternately displaying a first graphical user interface (first GUI) created by the first controller and a second graphical user interface (second GUI) created by the second controller, wherein:

first error information that is error information obtained from the first controller side and second error information that is error information obtained from the second controller side are shared by the first and second controllers, and are reflected on the first and second GUIs on the basis of the first and second error information.

BRIEF DESCRIPTION OF THE DRAWINGS

FIG. 7 shows error levels according to the present embodiment;

FIG. 8 shows differences of register positions according to error levels when error information is registered on error information output table Tb1 according to the present embodiment;

DESCRIPTION OF THE PREFERRED EMBODIMENTS

Figure 1:
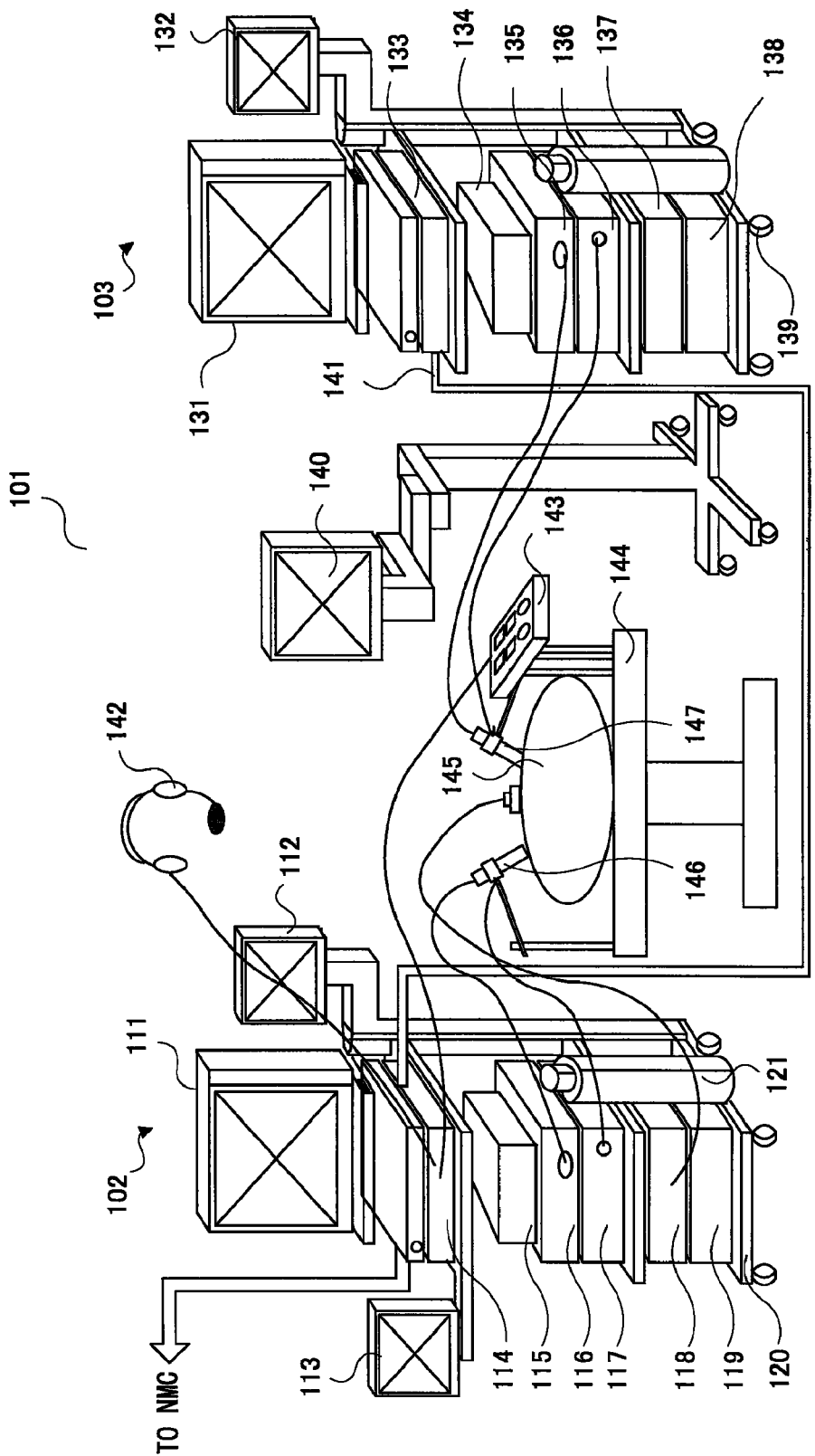
FIG. 1 shows an entire configuration of the medical device control system according to the present embodiment.

Hereinafter, the embodiments of the present invention will be explained in detail, referring to the drawings.

A medical support control system according to the present embodiment includes a medical device control system and a non-medical device control system. The medical device control system includes a plurality of medical devices and a medical controller for controlling these medical devices. The non-medical device control system includes non-medical devices (that may further include medical devices) that are used for operations, and a non-medical controller for controlling these non-medical devices.

An endoscopic operating system will be explained as an example of the medical device control system.

FIG. 1 shows an entire configuration of the medical device control system according to the present embodiment. An endoscopic operating system is shown as a medical device control system 101. In the operating room, a first endoscopic operating system 102 and a second endoscopic operating system 103 beside a bed 144 on which a patient 145 is laid and a wireless remote controller 143 for the operating person are provided.

The endoscopic operating systems 102 and 103 respectively have first and second trolleys 120 and 139 each including a plurality of endoscope peripheral devices used for observation, examination, procedures, recoding, and the like. Also, an endoscope image display panel 140 is arranged on a movable stand.

On the first trolley 120, an endoscope image display panel 111, a central display panel 112, a central manipulation panel device 113, a medical controller (MC) 114, a recorder 115, a video processor 116, an endoscope light source device 117, an insufflation unit 118, and an electrical surgical device 119 are arranged.

The central manipulation panel device 113 is arranged in an unsterilized area to be used by nurses or the like in order to manipulate the respective medical devices in a centralized manner. This central manipulation panel device 113 may include a pointing device such as a mouse, a touch panel, or the like (not shown). By using the central manipulation panel device 113, the medical devices can be managed, controlled, and manipulated in a centralized manner.

The respective medical devices are connected to the MC 114 via communication cables (not shown) such as serial interface cables or the like, and can have communications with one another.

Also, a headset-type microphone 142 can be connected to the MC 114. The MC 114 can recognize voices input through the headset-type microphone 142, and can control the respective devices in accordance with the voices of the operating person.

The endoscope light source device 117 is connected to a first endoscope 146 through a light-guide cable used for transmitting the illumination light. The illumination light emitted from the endoscope light source device 117 is provided to the light guide of the first endoscope 146 and illuminates the affected areas or the like in the abdomen of the patient 145 into which the insertion unit of the first endoscope 146 has been inserted.

The optical image data obtained through the camera head of the first endoscope 146 is transmitted to a video processor 116 through a camera cable. The optical image data undergoes signal processing in a signal processing circuit in the video processor 116, and the video signals are created.

The insufflation unit 118 provides $CO_2$ gas to the abdomen of the patient 145 through a tube. The $CO_2$ gas is obtained from a gas tank 121.

On the second trolley 139, an endoscope image display panel 131, a central display panel 132, a expansion unit 133, a recorder 134, a video processor 135, an endoscope light source device 136, and other medical devices 137 and 138 (such as an ultrasonic processing device, a lithotripsy device, a pump, a shaver, and the like) are arranged. These respective devices are connected to the expansion unit 133 through cables (not shown), and can communicate with one another. The MC 114 and the expansion unit 133 are connected to each other through the expansion cable 141.

The endoscope light source device 136 is connected to a second endoscope 147 through the light-guide cable for transmitting the illumination light. The illumination light emitted from the endoscope light source device 136 is provided to the light guide of the second endoscope 147, and illuminates the affected areas or the like in the abdomen of the patient 145 into which the insertion unit of the second endoscope 147 has been inserted.

The optical image data obtained through the camera head of the second endoscope 147 is transmitted to a video processor 135 through a camera cable. The optical image data undergoes signal processing in a signal processing circuit in the video processor 135, and the video signals are created. Then, the video signals are output to the endoscope image display panel 131, and endoscope images of the affected areas or the like are displayed on the endoscope image display panel 131.

Further, the MC 114 can be controlled by the operating person manipulating the devices in the unsterilized area. Also, the first and second trolleys 120 and 139 can include other devices such as printers, ultrasonic observation devices, or the like.

Figure 2:
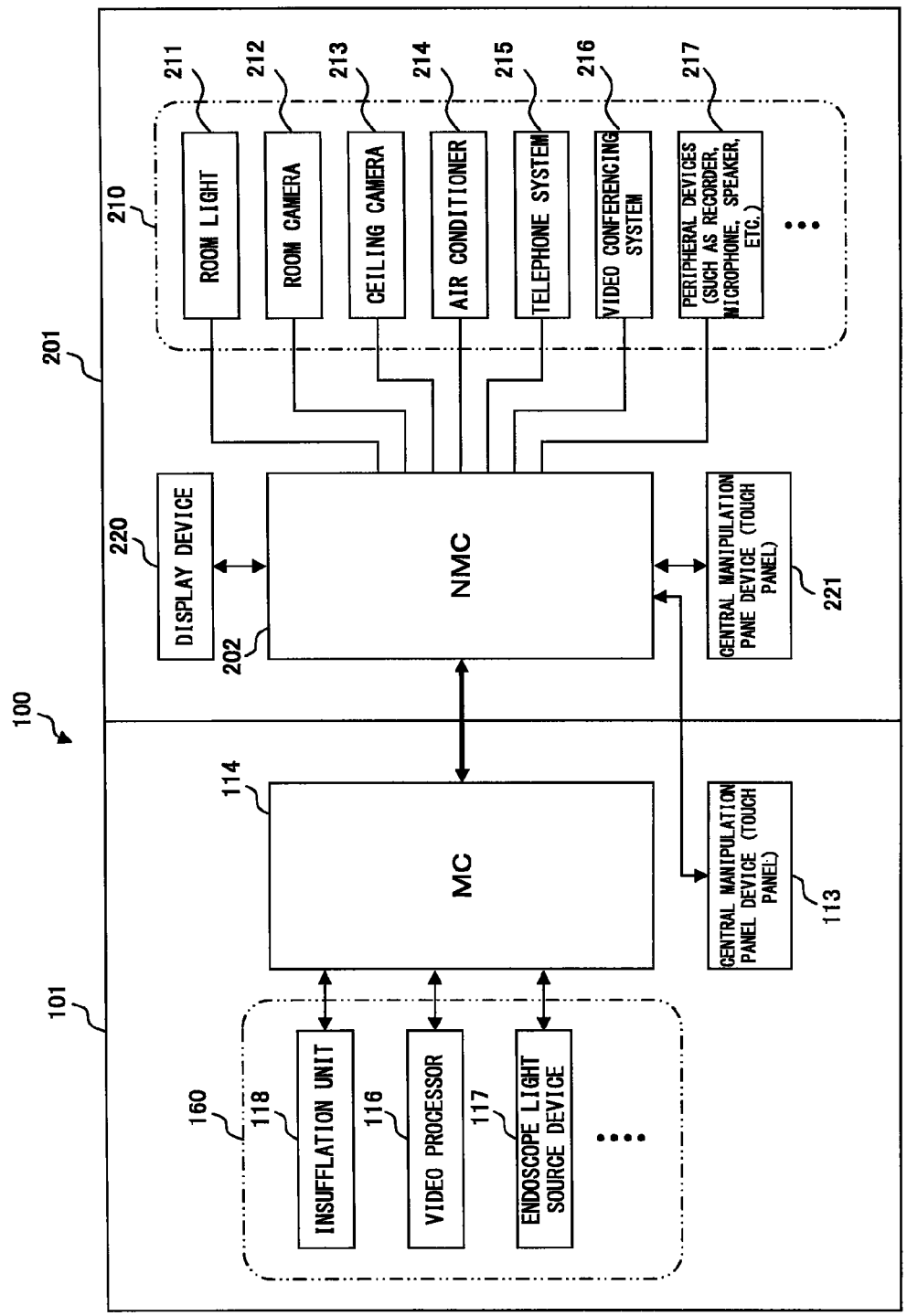
FIG. 2 is a block diagram showing an entire configuration of a medical support control system 100 according to the present embodiment.

FIG. 2 is a block diagram showing an entire configuration of a medical support control system 100 according to the present embodiment. As described above, the medical support control system 100 includes the medical device control system 101 and a non-medical device control system 201. A detailed configuration of the medical device control system 101 is as shown in FIG. 1. However, in FIG. 2, the medical device control system 101 is shown in a simplified manner for simplicity of explanation.

In FIG. 2, a medical device group 160 is a group of medical devices that are directly connected to the medical controller 114 or are indirectly connected to the MC 114 via the expansion unit 133. Examples of the devices included in the medical device group 160 are the insufflation unit 118, the video processor 116, the endoscope light source device 117, the electrical surgical device 119, and the like.

The central manipulation panel device 113 has a touch panel, and in accordance with the information input into the touch panel, the devices connected to the MC 114 or a non-medical device controller (NMC) 202 that will be described later can be manipulated.

The non-medical control system 201 includes the NMC 202 connected to the MC 114 through a communication cable or the like, and a non-medical device group 210. In this configuration, the NMC 202 can transmit and receive, through an image cable, the video signals to and from the medical device group 160 connected to the MC 114.

The NMC 202 controls the non-medical devices (including the audio-visual devices) connected thereto. As shown in FIG. 2, the non-medical device group 210 connected to the NMC 202 according to the present embodiment consists of a room light 211, a room camera 212, a ceiling camera 213, an air conditioner 214, a telephone system 215, a conference system 216 to be used for individuals in remote places (referred to as a video conference system hereinafter), and other peripheral devices 217. Further, a display device 220 and a central manipulation panel device 221 are connected to the NMC 202.

Also, the non-medical device group 210 includes equipment such as light devices provided in the operating room in addition to the AV devices used for recording and reproducing image data.

The display device 220 is a plasma display panel (PDP) or a liquid crystal display (LCD) device, and displays images of the predetermined device or images of the devices selected by nurses or the like through the central manipulation panel device 221. The room light 211 is a device that illuminates the operating room. The room camera 212 is used for shooting images of the situations in the operating room. The ceiling camera 213 is a camera suspended from the ceiling whose positions can be changed. The conference system 216 is a system that displays images and transmits voices of nurses or the like in the medical office or the nurse stations, and enables conversations with them. The peripheral devices 217 are, for example, a printer, a CD player, a DVD recorder, and the like. The central manipulation panel device 221 has a touch panel that is the same as that included in the central manipulation panel device 113, and controls the respective AV devices connected to the NMC 202. The central manipulation panel devices 113 and 221 are referred to as TPs hereinafter.

Figure 3:
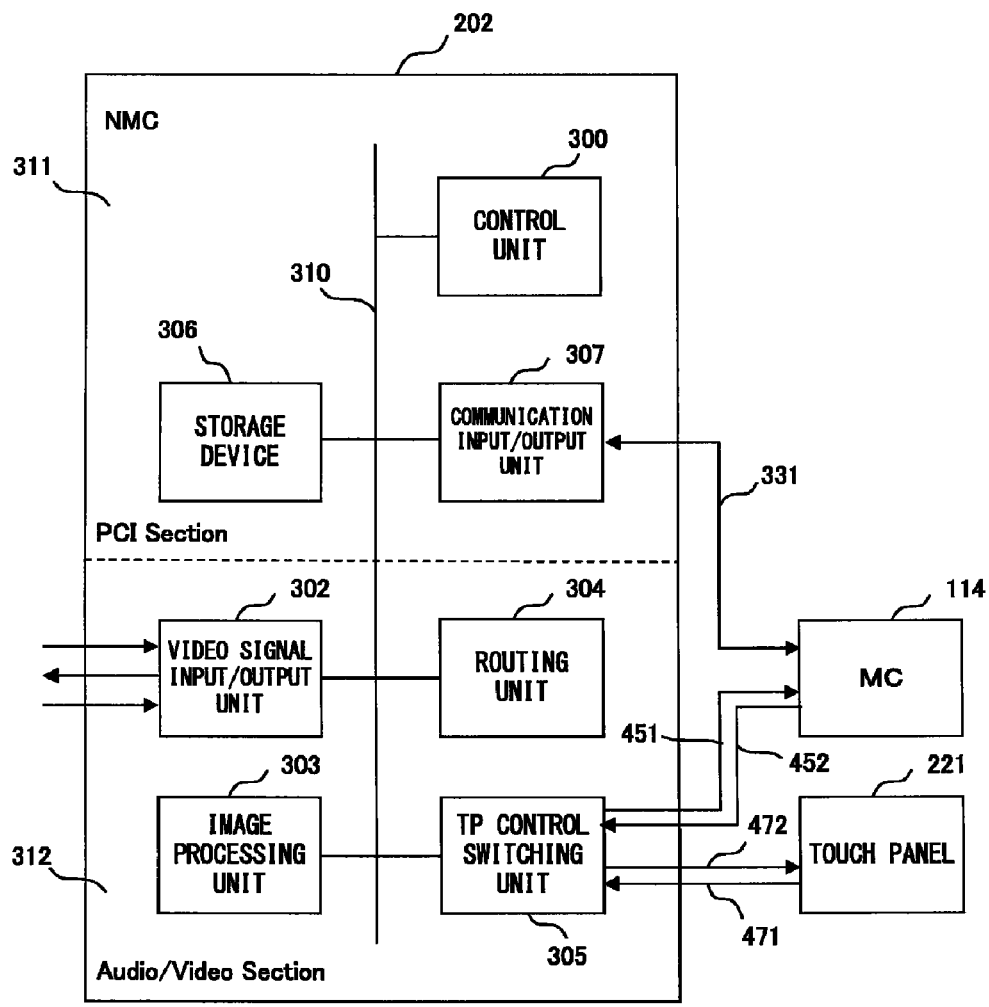
FIG. 3 is a block diagram showing a configuration of a NMC 202 according to the present embodiment.

FIG. 3 is a block diagram showing a configuration of the NMC 202 in the present embodiment. The NMC 202 includes a PCI section 311 and an audio/video (A/V) section 312.

The PCI section 311 mainly controls a non-medical device group 210 connected to the NMC 202. The PCI section 311 includes a control unit 300, a storage device 306, and a communication input/output unit 307. Numeral 310 denotes a back plane.

The control unit 300 controls the entirety of the PCI section 311, and transmits and receives data to and from the A/V section 312. The control unit 300 creates Graphical User Interface image information (hereinafter, referred to as GUI image information) that is an image layout to be displayed on a TP 221 or a monitor device, and transmits it to a routing unit 304. Also, as will be described later, the control unit 300 performs processes accompanying the data transmission/reception on the based of the communication with the MC 114 via a communication line 331. The NMC 202 and the MC 114 monitor each other via the communication line 331, and synchronize each other's GUI environment.

The storage device 306 stores various programs, information set by the TP 221, and the like. The communication input/output unit 307 is a communication interface used for the communications with the MC 114 via a communication line 331.

The A/V section 312 is a section that mainly processes the video signals and the audio signals. The A/V section 312 includes a video signal input/output unit 302, an image processing unit 303, a routing unit 304, and a TP control switching unit 305.

The video signal input/output unit 302 has a plurality of video signal input ports and a plurality of video signal output ports.

The routing unit 304 switches routes for the video signals that were processed in the image processing unit 303 and the video signals input from the video signal input/output unit 302, and transfers them to a prescribed configuration unit in the NMC 202. Also, the routing unit 304 transfers to the TP control switching unit 305 the GUI image information created in the control unit 300.

The image processing unit 303 performs image processing on the image information transferred from the routing unit 304. Examples of the image processing are the enlargement/reduction (scaling) of images, the mirroring of images, the rotation of images, displaying another, smaller image in a main image (picture in picture (PIP)), and displaying a plurality of images simultaneously (picture out picture (POP)).

TP coordinate communication lines 451 and 471 are communication lines through which TP coordinate signals generated by touch manipulations on the TP 221 are conveyed. TP image lines 452 and 472 are image lines through which image signals such as GUI images or the like to be displayed on the TP 221 are conveyed.

The TP control switching unit 305 synthesizes the GUI image created in the control unit 300 with images created on the basis of the video signals transmitted from the video signal input/output unit 302. Then, the TP control switching unit 305 outputs the synthesized image to the TP 221. Further, the TP control switching unit 305 can perform switching between the NMC 202 and the MC 114 as the manipulation targets of the TP 221. In other words, the TP control switching unit 305 receives TP coordinate information from the TP 221 based on touch manipulations on the TP 221, transfers the received TP coordinate information to the control unit 300, or transfers the TP coordinate information to the MC 114.

Figure 4A:
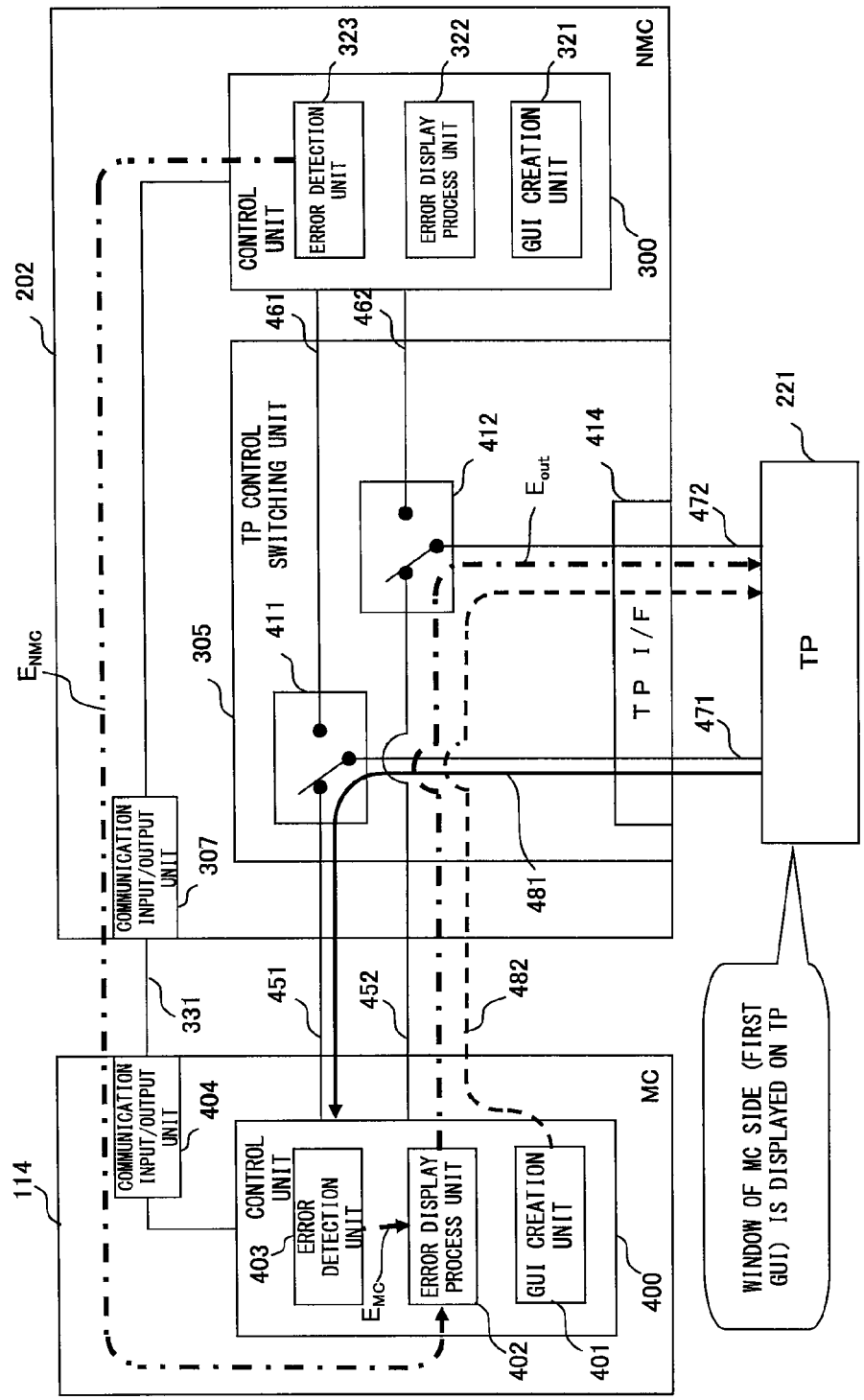
FIG. 4A is a first view showing switching of a control target performed by a TP control switching unit 305 between the NMC 202 and the MC 114 according to the present embodiment.
Figure 4B:
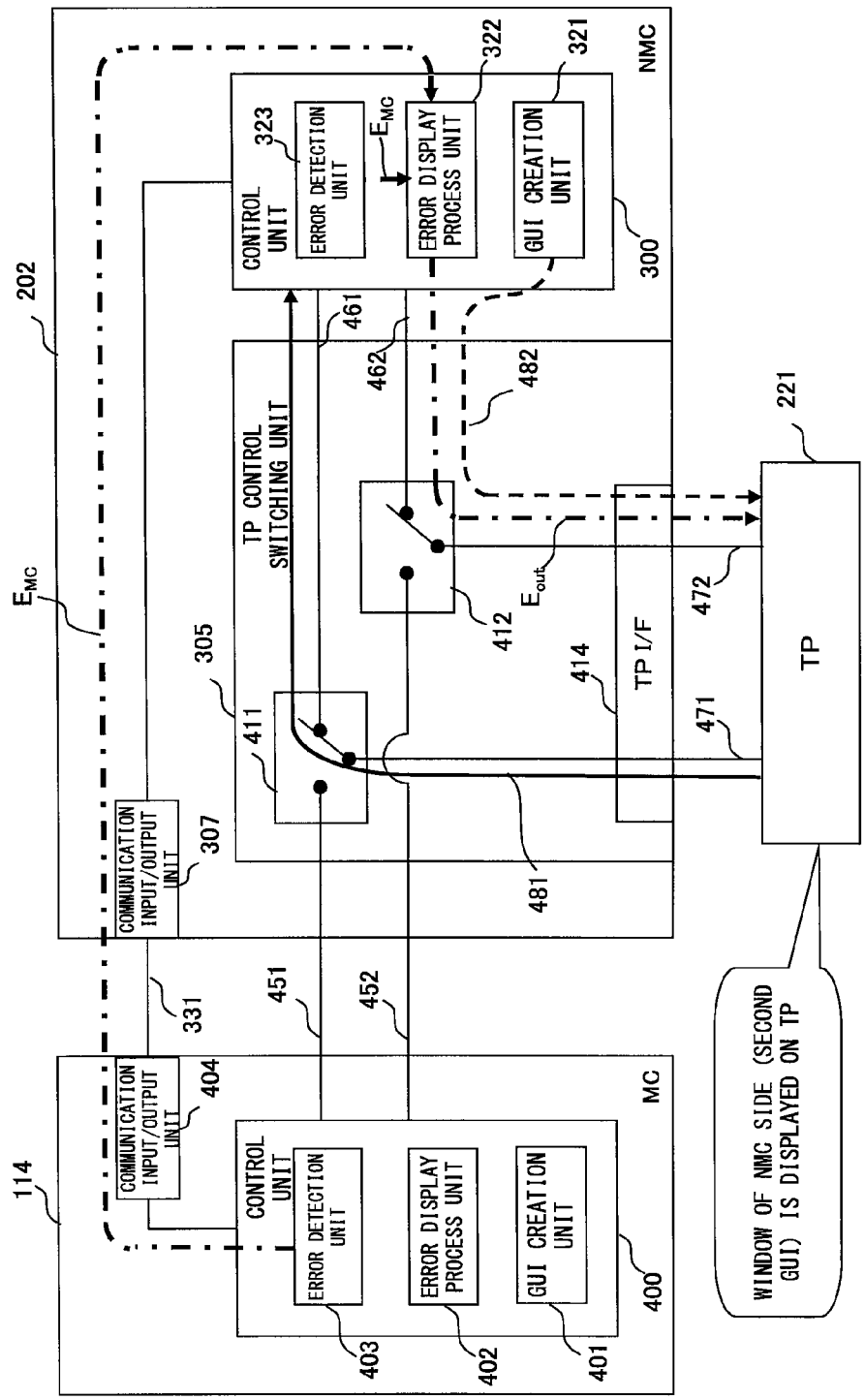
FIG. 4B is a second view showing switching of a control target performed by the TP control switching unit 305 between the NMC 202 and the MC 114 according to the present embodiment.

FIGS. 4A and 4B respectively show the switching of the control targets between the NMC 202 and the MC 114 by using the TP control switching unit 305.

As described above, the MC 114 is a controller mainly for the medical devices. The MC 114 creates a graphical user interface (first GUI) that is a window used for controlling the medical devices.

As described above, the NMC 202 is a controller mainly for the non-medical devices. The NMC 202 creates a graphical user interface (second GUI) that is a window used for controlling the non-medical devices.

The first and second GUIs are designed on the basis of a common graphical user interface (common GUI). For example, by switching the tabs on a window on the TP 221, the first and second GUIs can be switched there between.

The control unit 300 has a GUI creation unit 321, an error display process unit 322, and an error detection unit 323. The GUI creation unit 321 creates the second GUI.

The error detection unit 323 detects error information $E_{NMC}$ caused on the NMC 202 side. The error information $E_{NMC}$ is error information about, for example, devices connected to the NMC 202 and is error information caused in the NMC 202.

The error display process unit 322 obtains the error information $E_{NMC}$ caused on the NMC 202 side and the error information $E_{MC}$ caused on the MC 114 side, and outputs to the TP 221 error information $E_{out}$ determined on the basis of a process flow (which will be described later)

The control unit 400 has a GUI creation unit 401, an error display process unit 402, and an error detection unit 403. The GUI creation unit 401 creates a first GUI.

The error detection unit 403 detects error information $E_{MC}$ on the MC 114 side. The error information $E_{MC}$ is error information about, for example, devices connected to the MC 114 and is error information caused in the MC 114.

The error display process unit 402 obtains the error information $E_{NMC}$ caused on the NMC 202 side and the error information $E_{MC}$ caused on the MC 114 side, and outputs to the TP 221 the error information $E_{out}$ determined on the basis of the process flow (which will be described later).

The TP coordinate communication lines 451, 461, and 471 are communication lines for transmitting TP coordinate signals from the TP 221 to the control unit 400 of the MC 114 or to the control unit 300 of the NMC 202.

The TP image lines 452, 462, and 472 are image lines for transmitting video signals such as a first or second GUI image to be displayed on the TP 221 from the control unit 400 of the MC 114 to the TP 221 or from the control unit 300 of the NMC 202 to the TP 221. Also, the error information $E_{out}$ is also output via the TP image lines 452, 462, and 472.

The TP control switching unit 305 has a TP coordinate communication line switch 411, a TP image line switch 412, and a TP I/F 414.

The TP I/F 414 is an interface to which the TP image line and the TP coordinate communication line between the TP 221 and the NMC 202 are connected.

The TP coordinate communication line switch 411 is a switch that determines whether the TP coordinate communication line 471 is to be connected to the TP coordinate communication line 451 of the MC 114 side or the TP coordinate communication line 461 of the NMC 202 side.

The TP image line switch 412 is a switch that determines whether the TP image line 472 is to be connected to the TP image line 452 of the MC 114 side or the TP image line 462 of the NMC 202 side.

A communication input/output unit 404 is a communication interface used for performing communications with the NMC 202 via the communication line 331.

Explanations will be given for a case, shown in FIG. 4A, in which the TP coordinate communication line 451 is selected by the switch 411 and the TP image line 452 is selected by the switch 412. A TP image signal 482 created by the GUI creation unit 401 is input into the TP 221 via the switch 412, and the first GUI is displayed on the TP 221. In this case, a TP coordinate signal 481 caused by touch manipulations on the first GUI displayed on the TP 221 is input into the control unit 400 from the TP 221 via the switch 411.

In the case shown in FIG. 4A, the error detection unit 403 detects the error information $E_{MC}$ caused on the MC 114 side, and reports the error information $E_{MC}$ to the error display process unit 402. Also, the error detection unit 323 detects the error information $E_{NMC}$ caused on the NMC 202 side, and reports the error information $E_{NMC}$ to the error display process unit 402 via the communication line 331. In this case, "error information $E_g$" represents the error information $E_{MC}$ and the error information $E_{NMC}$ obtained by the error display process unit 402. The error display process unit 402 determines which error information has the highest priority from among the error information $E_g$ on the basis of the priority order set in advance, and outputs the information determined to have the highest priority as information $E_{out}$ to the TP 221. On the TP 221, the error information $E_{out}$ is displayed. If there are a plurality of pieces of information that have the highest priority, such pieces of information are displayed on the TP 221 sequentially and repeatedly at constant time intervals.

Next, explanations will be given for a case, shown in FIG. 4B, in which the TP coordinate communication line 461 is selected by the switch 411, and the TP image line 462 is selected by the TP image line switch 412. The TP image signal 482 created by the GUI creation unit 401 is input into the TP 221 via the switch 412, and the second GUI is displayed on the TP 221. The TP coordinate signal 481 caused by the touch manipulations on the second GUI displayed on the TP 221 is input from the TP 221 into the control unit 300 via the switch 411.

In the case shown in FIG. 4B, the error detection unit 323 detects the error information $E_{NMC}$ caused on the NMC 202 side, and reports the error information $E_{NMC}$ to the error display process unit 402. Also, the error detection unit 403 detects the error information $E_{MC}$ caused on the MC 114 side, and reports the error information $E_{MC}$ to the error display process unit 322 via the communication line 331. In this case, "error information $E_g$" represents the error information $E_{MC}$ and the error information $E_{NMC}$ obtained by the error display process unit 322. The error display process unit 322 determines which error information has the highest priority from among the error information $E_g$ on the basis of the priority order set in advance, and outputs the information determined to have the highest priority as information $E_{out}$ to the TP 221. On the TP 221, the error information $E_{out}$ is displayed. If there are a plurality of pieces of information that have the highest priority, such pieces of information are displayed on the TP 221 sequentially and repeatedly at constant time intervals.

Next, explanations will be given for a case in which the first GUI transits to the second GUI in response to the touch manipulations on the TP 221. The TP coordinate signal 481 created by the touch manipulations on the TP 221 is sent to the control unit 400 in the MC 114. The control unit 400 that has received the TP coordinate signal 481 reports, to the control unit 300 in the NMC 202 via the communication line 331, that the first GUI will be switched to the second GUI. When receiving this report, the control unit 300 controls the TP control switching unit 305, and the switches 411 and 412 are operated so that the TP coordinate communication line 461 and the TP image line 462 on the NMC 202 side are enabled. Then, the control unit 300 causes the TP 221 to display the second GUI via the TP image lines 462 and 472. Additionally, this process is also applied to the case in which the second GUI transits to the first GUI in response to the touch manipulations.

The control units 300 and 400 monitor each other via the communication line 331. Also, the control units 300 and 400 synchronize each other's GUI environment via the communication line 331, and exchange information that has to be held by both of them for configuring a common GUI. An example of the above information is window elements (window element information such as tab names) to be used commonly.

As described above, the target to be controlled by the TP 221 is changed between the MC 114 and the NMC 202 on the basis of the switching operations of the TP control switching unit 305. This switching operation is not perceived by the users, and accordingly the users feel as if they have controlled only one controller.

Figure 5:
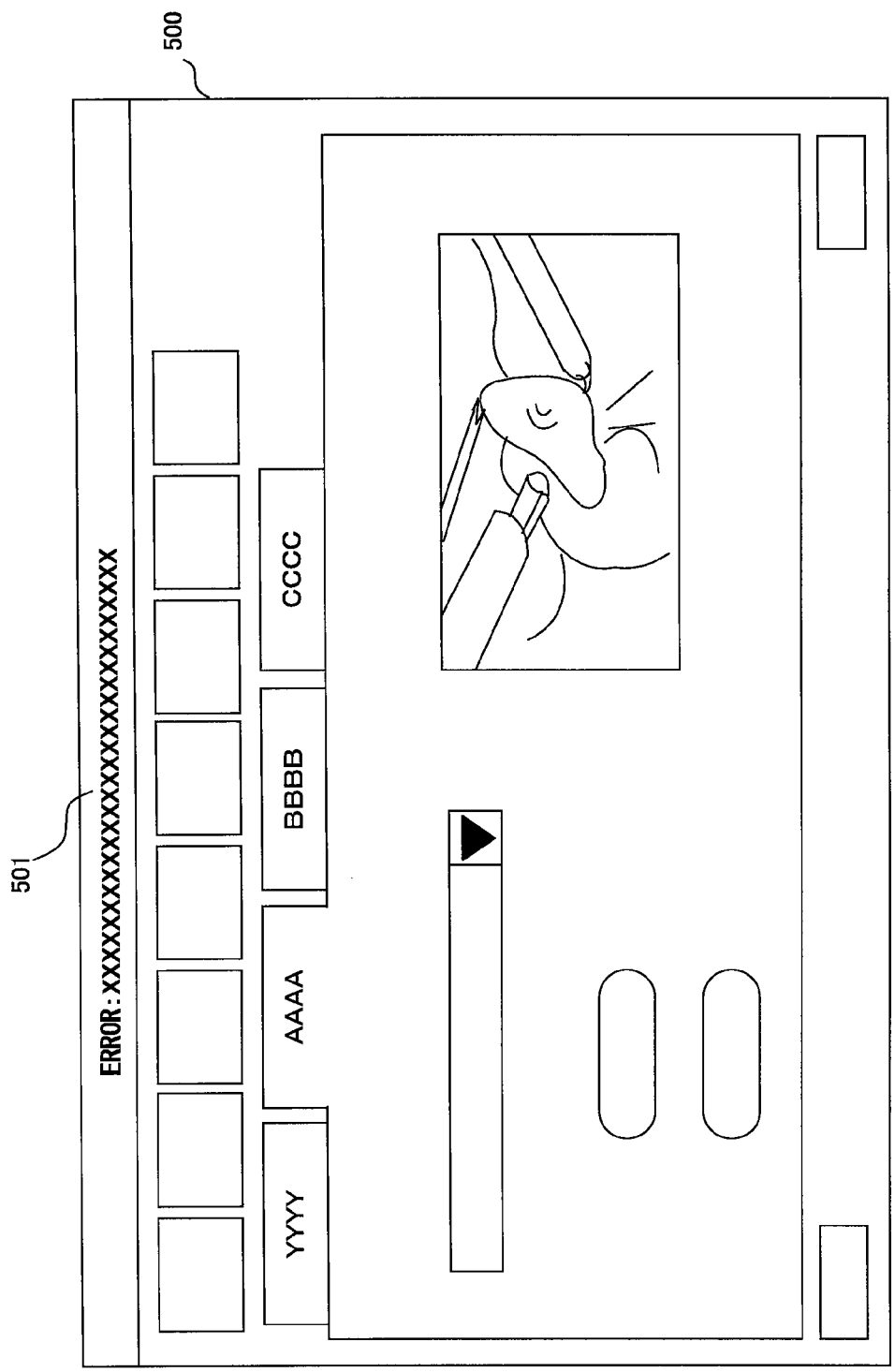
FIG. 5 shows an example of an error display displayed on an operation window according to the present embodiment.

FIG. 5 shows an example of an error display displayed on an operation window according to the present embodiment. An operation window 500 is displayed on the TP 221 on the basis of the common GUI. As explained by referring to FIGS. 4A and 4B, when the error information $E_{out}$ is output from the MC 114 or the NMC 202, the error display is displayed in an error display area 501 located on an upper portion of the operation window 500 on the basis of the error information $E_{out}$.

Figure 6:
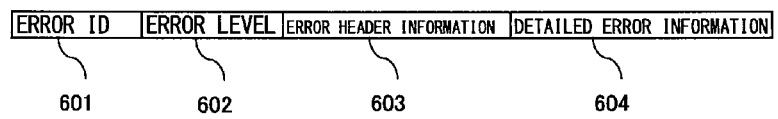
FIG. 6 shows an example of the data structure of error information $E_g$ according to the present embodiment.

FIG. 6 shows an example of a data structure of the error information $E_g$ according to the present embodiment. The error information $E_g$ includes an "error ID" 601, an "error level" 602, "error header information" 603, and "error detailed information" 604. The "error ID" 601 is an ID used for identifying the error information $E_g$. The "error level" 602 is an error level according to the importance of each error (level S, level A, and level B). The "error header information" 603 is simplified information about each error, and is displayed on the error display area 501. The "error detailed information" 604 is detailed information about each error.

FIG. 7 shows the respective error levels according to the present embodiment. There are level S, level A, and level B, starting from the level of the highest priority. Level S represents a critical error that requires a turn-off of the system. Level A represents a warning. Level B represents caution.

The priority order is the order of displaying the pieces of information. If an error $E_H$ is caused when other error information $E_R$ of a lower priority order is being displayed (case 1), the error information $E_H$ of the higher priority order is displayed. If error information $E_S$ is caused when error information $E_R$ of the same priority order is being displayed (case 2), $E_S$ and $E_R$ are displayed sequentially and repeatedly. If error $E_L$ is caused when an error $E_R$ of a higher priority order is being displayed (case 3), the error $E_L$ of the lower priority order is not displayed unless the error $E_R$ is cancelled.

When a level S error is caused, only the error information of that error is continuously displayed on the error display area 501, and all the operations and all the communications with other devices are stopped. Also, even if a prescribed button (for example, a "Help" button or the like) is not pressed, the content of the "error detailed information" 604 is displayed on the central portion of the TP 221 and the display panel window.

If a level A error is caused when a level B error is being displayed, the level A error information is displayed on the error display area 501. The level B error is not displayed on the error display area 501 until the level A error is cancelled.

If another level A error is caused when a level A error is being displayed, the latest level A error is displayed on the error display area 501 for "n" seconds (n is an integer set arbitrarily). Thereafter, the other pieces of level A error information are displayed sequentially. This is also applied to a case when a level B error is newly caused when a level B error is being displayed.

FIG. 8 shows how the registered positions change according to error levels when registration is made on an error information output table Tb1. The error information output table Tb1 is stored in a prescribed storage device in the TP control switching unit 305. The first table in FIG. 8 is a sample of the error information output table Tb1. On this error information output table Tb1, four pieces of level A error information are registered as records No. 1 through No. 4. The error information of record No. 3 is currently displayed. Thereafter, the records are sequentially and repeatedly displayed in the order of No. 4→No. 1→No. 2→No. 3→No. 4→No. 1→ . . . . The respective pieces of error information are displayed for "n" seconds. Hereinafter, cases 1-3 are explained by using this sample.

First explanation is given for a case in which an error $E_H$ is caused when error information $E_R$ of a lower priority order is being displayed (case 1). If a level S error is caused (error ID XX5) when a level A error is being displayed, the record of the level S error information is inserted into the top of the error information output table Tb1, and the records below the inserted position are respectively shifted to the lower positions. Then, the level S error information is output from the TP control switching unit 305 to the TP 221.

Next, explanation is given for a case in which an error $E_S$ is caused when error information $E_R$ of the same priority order is being displayed (case 2). If a level A error (error ID: XX5, VTR tape does not exist) is caused when level A error information of the same priority order (camera PC card error) is being displayed, the record of the error information of "error ID: XX6" is inserted into the position of record No. 3, and the records below that position are respectively shifted to the lower positions. Then, the error information of the record No. 3 that was newly inserted is displayed for n seconds. Thereafter, the records are sequentially and repeatedly displayed in the order of No. 4→No. 5→No. 1→No. 2→No. 3→No. 4→No. 5→No. 1 . . . .

Explanation is given for a case in which an error $E_L$ is caused when error information $E_R$ of a higher priority order is being displayed (case 3). If a level B error (error ID: XX7) is caused when a level A error is being displayed, the record of the level B error information is added to the bottom of the error information output table Tb1. In this case, the records are sequentially and repeatedly displayed in the order of No. 3→No. 4→No. 1→No. 2→No. 3→No. 4→No. 1 . . . . The level B error (error ID: XX7) is not displayed unless all the pieces of the level A error information are cancelled.

When errors are cancelled, the records of the pieces of error information corresponding to the cancelled errors are deleted from the error information output table Tb1, and the records that were below the deleted positions are respectively shifted to the upper positions in order to fill the deleted positions. When an error that is currently being displayed is deleted, the next error is displayed immediately.

Figure 9:
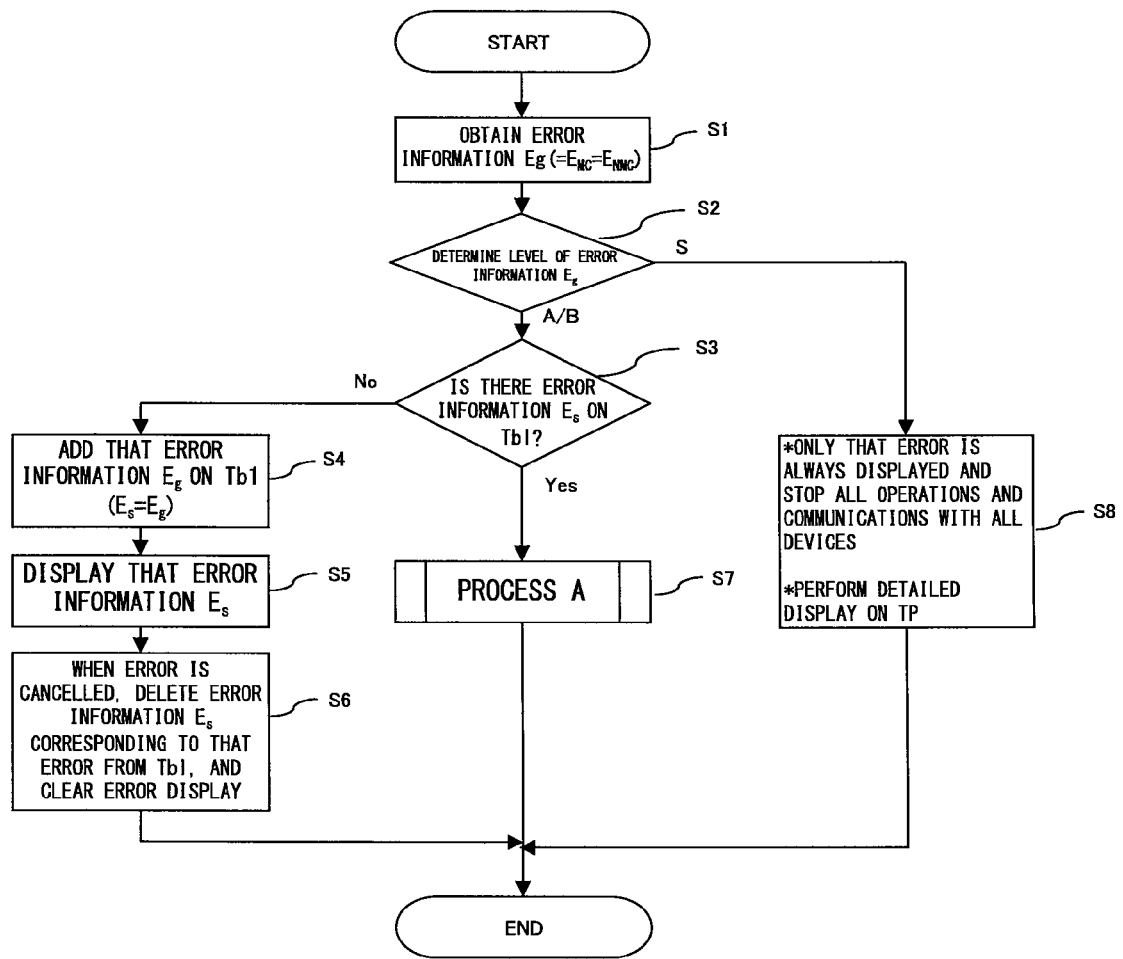
FIG. 9 is a flowchart for outputting error information according to the present embodiment.

FIG. 9 is a flowchart for outputting error information according to the present embodiment. The programs for the present embodiment are respectively stored in the storage devices in the MC 114 and the storage device 306 in the NMC 202. The control unit 300 and the control unit 400 respectively read the programs from their own storage devices, and execute the flowchart shown in FIG. 9. For simplicity of explanation, constituent elements of the controller that is selected as the control target by the TP 221 are represented by a control unit Ca, an error detection unit C1a, an error display process unit C2a, and a GUI creation unit C3a, and constituent elements of the other controller are represented by a control unit Cb, an error detection unit C1b, an error display process unit C2b, and a GUI creation unit C3b.

Accordingly, in the case shown in FIG. 4A, the control unit 400, the error detection unit 403, the error display process unit 402, and the GUI creation unit 401 respectively correspond to Ca, C1a, C2a, and C3a. Also, the control unit 300, the error detection unit 323, the error display process unit 322, and the GUI creation unit 321 respectively correspond to Cb, C1b, C2b, and C3b.

Also, in the case shown in FIG. 4B, the control unit 300, the error detection unit 323, the error display process unit 322, and the GUI creation unit 321 respectively correspond to Ca, C1a, C2a, and C3a. Also, the control unit 400, the error detection unit 403, the error display process unit 402, and the GUI creation unit 401 respectively correspond to Cb, C1b, C2b, and C3b.

First, the error display process unit C2a obtains the error information $E_{MC}$ and $E_{NMC}$ detected in the error detection units C1a and C1b (S1). The error display process unit C2a determines the error levels of the obtained error information $E_g$ ($=E_{MC}=E_{NMC}$) (S2).

When it is determined in S2 that the error level is level S, the error display process unit C2a causes only that error to be displayed, and stops all the operations and all the communications with other devices. Further, details of that error are displayed on the TP 221 (S8).

When it is determined in S2 that the error level is level A/B, the error display process unit C2a determines whether there is error information $E_S$ that is registered currently in the error information output table Tb1 (S3).

When there is no error information $E_e$ that is registered currently on the error information output table Tb1 (No in S3), the error display process unit C2a adds the obtained error information $E_g$ to the error information output table Tb1 (S4), and outputs it to the TP 221 (S5). When the error is cancelled, the error display process unit C2a deletes from Tb1 the error information $E_e$ corresponding to the cancelled error, and clears the display of the error on the TP 221 (S6).

When there is error information $E_S$ currently registered on the error information output table Tb1 (Yes in S3), the error display process unit C2a performs process A (S7). Process A is explained in FIG. 10.

Figure 10:
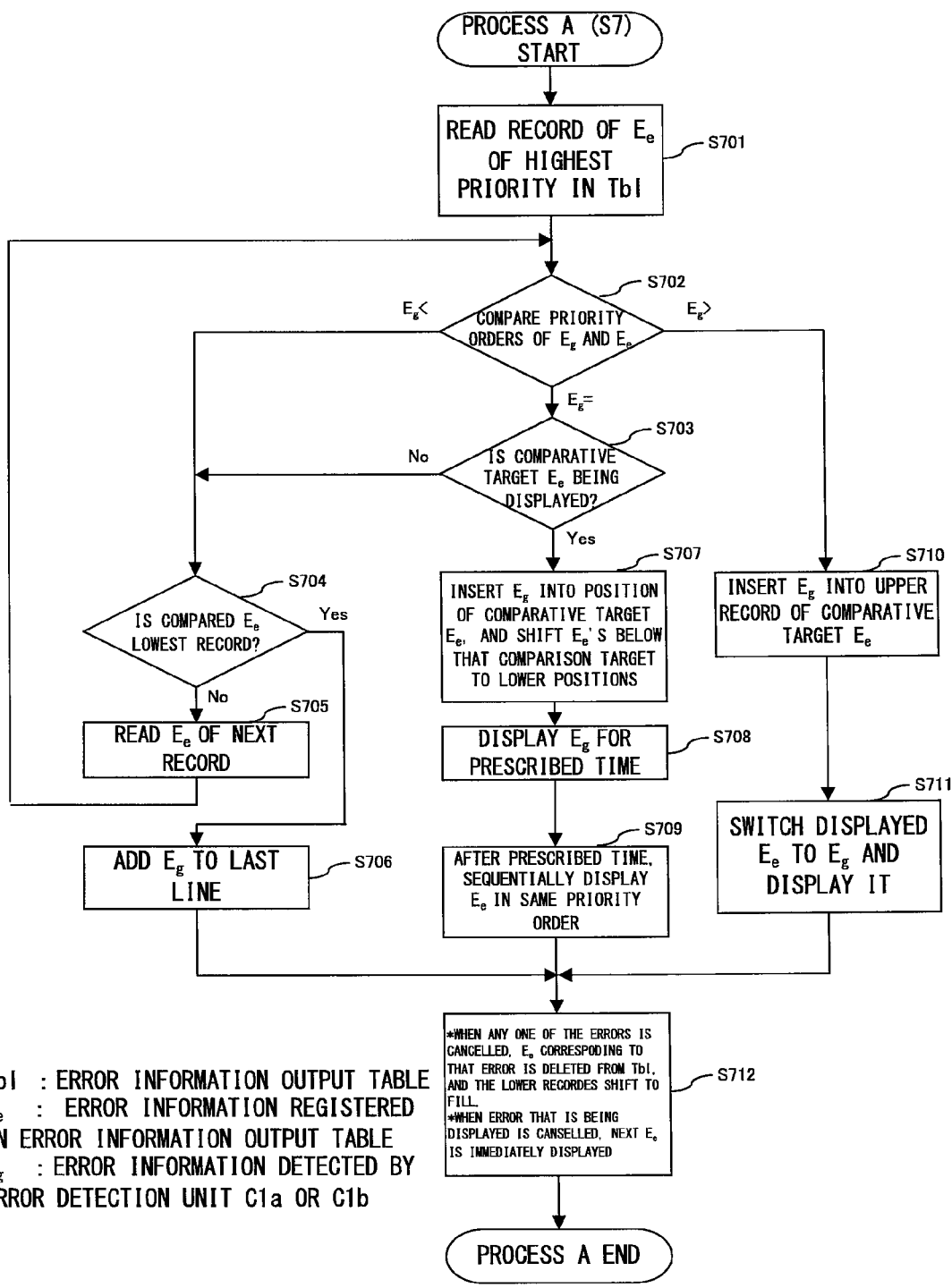
FIG. 10 shows, in detail, process A (S7) in FIG. 9.

FIG. 10 shows, in detail, process A (S7) shown in FIG. 9. The error display process unit C2a reads the error information Es of the top record in the error information output table Tb1 (S701), and executes the processes described below.

First, the priority order of the obtained error information $E_g$ and the priority order of the error information $E_e$ read from the error information output table Tb1 are compared to each other (S702). When $E_g<E_e$ is satisfied in S702, the record of the error information $E_g$ is added (S706) to the record next to the error information $E_e$ on the condition that the error information $E_e$ that was compared with was the lowest record (Yes in S704). If the error information $E_e$ that was compared with was not the lowest record (No in S704), the error information $E_e$ of the next record is read (S705), and the process of S702 is executed.

When $E_g=E_e$ is satisfied in S702, the process proceeds to S704 on the condition that the error information $E_e$ as a comparative target is not displayed on the TP 221 (No in S703). When the comparative target $E_e$ is displayed on the TP 221 (Yes in S703), the error information $E_g$ is inserted into the record position of the comparative target $E_e$, and the records below the inserted record are respectively shifted to the lower positions (S707).

The inserted error information $E_g$ is displayed for a prescribed time on the TP 221 (S708). After a prescribed time has elapsed, pieces of error information $E_e$ that are of the same priority order are respectively displayed for a prescribed time on the TP 221 (S709).

When $E_g>E_e$ is satisfied in S702, the record of the error information $E_g$ is inserted into the position before the record of the comparative target $E_e$ (S710). Then, the error information $E_e$ being currently displayed on the TP 221 is switched to the error information $E_g$ to be displayed (S711).

When any one of the errors is cancelled, the record of the error information $E_e$ corresponding to the cancelled error is deleted, and the records below the record of the cancelled error are respectively shifted to the upper positions. Also, when the error that is currently displayed is cancelled, the next error information $E_e$ is immediately displayed (S712).

As described above, the medical support control system according to the present embodiment includes the first controller (MC 114) connected to at least one device, the second controller (NMC 202) connected to at least one device, and the manipulation display device (TP 221).

The manipulation device (TP 221) is shared by the first controller and the second controller. The manipulation display device (TP 221) can alternately display the first graphical user interface (first GUI) created by the first controller and the second graphical user interface (second GUI) created by the second controller.

In the medical support control system, the first and second controllers share the first error information ($E_{MC}$), which is error information obtained from the first controller side, and the second error information ($E_{NMC}$), which is error information obtained from the second controller side. Further, the medical support control system can reflect the first and second error information on the first and second GUIs on the basis of the content of the first and second error information. The first and second information has priority order information and error content information representing the content of an error.

The error content information of the error information of the highest priority order among the obtained error information is displayed on the manipulation display device. If the priority order of the obtained pieces of error information are the same, the pieces of error content information of the error information of the same priority orders are sequentially switched to be displayed on the manipulation devices.

According to the present embodiment, not only can errors caused in the controller that is the control target of the TP 221 be displayed, but errors caused in the controller that is not the control target of the TP 221 can also be displayed.

The scope of the present invention is not limited to any of the above embodiments, and various other configurations and embodiments are allowed without departing from the spirit of the present invention.

As described above, it is possible to provide a medical support control device for controlling medical devices and non-medical devices.

What is claimed is:

1. A medical support control system comprising:
a first controller connected to at least one device and comprising a first GUI generation unit that generates a first graphical user interface (first GUI);
a second controller connected to at least one device and comprising a second GUI generation unit that generates a second graphical user interface (second GUI);
a manipulation display device shared by the first controller and the second controller, and alternately displaying the first GUI created by the first GUI generation unit and the second GUI created by the second GUI generation unit; and
a communication line connecting the first and second controllers to each other,
wherein
the first controller comprises:
a first error detection unit configured to detect first error information that relates to an error caused in the first controller and an error caused in the device connected to the first controller,
a first transmission unit configured to transmit the first error information detected by the first error detection unit to the second controller via the communication line,
a first reception unit configured to receive second error information from the second controller via the communication line, wherein the second error information is information that relates to an error caused in the second controller and an error caused in the device connected to the second controller,
a first error information share unit configured to share the first error information detected by the first error detection unit and the second error information received from the second controller, and
a first error information output unit configured to output the first and second error information shared by the first error information share unit, and wherein
the second controller comprises
a second error detection unit configured to detect the second error information that relates to the error caused in the second controller and the error caused in the device connected to the second controller,
a second transmission unit configured to transmit the second error information detected by the second error detection unit to the first controller via the communication line,
a second reception unit configured to receive the first error information detected by the first error detection unit from the first controller via the communication line,
a second error information share unit configured to share the second error information detected by the second error detection unit and the first error information received from the second reception unit,
a second error information output unit configured to output the first and second error information shared by the second error information share unit, and
a switching unit configured to select the first or second error information output unit on the basis of a touch manipulation on the manipulation display device and to route the first or second error information output from the selected first or second error information output unit to the manipulation display device, and
wherein
the first and second error information share units each hold error information detected by the error detection unit of the other controller,
the first and second error information include an error level, with error simplified information representing a simplified content relating to an error, and error detailed information representing a detailed content relating to the error; and
the first and second error information share units each comprise:
an error obtainment unit configured to obtain the first or second error information detected by the first or second error detection unit,
a first error level determination unit configured to determine the error level of the first or second error information obtained by the error obtainment unit, and
a first error level process unit configured to cause the manipulation display device to display the error detailed information of the first or second error information, when a result of the determination by the first error level determination unit indicates that the determined error level is a highest error level.

2. The medical support control system according to claim 1, wherein:
- the first and second error information include an error level and error content information representing the content of an error; and
- the first and second error information output units each comprise:
  - an error level determination unit configured to determine extent of error levels of the first and second error information shared by the first and second error information share units, and
  - an error content information output unit configured to output the error content information of error information which includes a highest error level among the first and second error information, wherein the highest error level is determined by the error level determination unit.

3. The medical support control system according to claim 2, wherein
when a result of the determination by the error level determination unit indicates that the error levels of the shared first and second error information are the same, the error content information output unit causes the manipulation display device to display pieces of the error content information of pieces of the error information of the same level in such a way that the display of one of the pieces of the error content information is sequentially switched to the display of the other.

4. The medical support control system according to claim 1, wherein
the error content information output unit further comprises
- an error information output table in which the first or second error information obtained by the error obtainment unit is registered,
- an error information output table reading unit configured to read the first or second error information registered in the error information output table,
- a second error level determination unit configured to determine the error level of the first or second error information obtained by the error obtainment unit and the error level of the first or second error information read by the error information output table reading unit when a result of the determination by the first error level determination unit indicates that the determined error level is not the highest error level, and
- a sequential display process unit, wherein, when a result of the determination by the second error level determination unit indicates that the error level of the first or second error information, obtained by the error obtainment unit and the error level of the first or second error information read from the error information output table are equal, the sequential display process unit causes the manipulation display device to sequentially display, for a predetermined period, the error simplified information of the first or second error information obtained by the error obtainment unit and pieces of the error simplified information of pieces of the error information of the same error level registered in the error information output table.

* * * * *